United States Patent
Khandelwal et al.

(10) Patent No.: US 11,919,853 B2
(45) Date of Patent: *Mar. 5, 2024

(54) PROCESS AND APPARATUS FOR PREPARING PURIFIED STYRENE COMPOSITION FROM STYRENE CONTAINING FEEDSTOCK

(71) Applicant: SULZER MANAGEMENT AG, Winterthur (CH)

(72) Inventors: Rahul Khandelwal, Katy, TX (US); Joseph C. Gentry, Houston, TX (US); Randi Wytcherley, Belgrade, MT (US); Kimberly Anderson, Bozeman, MT (US); Meta Naulita-Ellis, Bozeman, MT (US); Claudia Pudack, Zürich (CH); Celine Rioual, Chalampé (FR); Christoph Kirschner, Volketswil (CH); B. Bryant Slimp, Houston, TX (US); Manfred Stepanski, Buchs (CH); Erik Temmel, Basel (CH)

(73) Assignee: SULZER MANAGEMENT AG, Winterthur (CH)

(*) Notice: Subject to any disclaimer, the term of this patent is extended or adjusted under 35 U.S.C. 154(b) by 0 days.

This patent is subject to a terminal disclaimer.

(21) Appl. No.: 17/922,540
(22) PCT Filed: May 7, 2021
(86) PCT No.: PCT/EP2021/062208
§ 371 (c)(1),
(2) Date: Oct. 31, 2022
(87) PCT Pub. No.: WO2021/224483
PCT Pub. Date: Nov. 11, 2021

(65) Prior Publication Data
US 2023/0174441 A1    Jun. 8, 2023

Related U.S. Application Data
(60) Provisional application No. 63/022,109, filed on May 8, 2020.

(30) Foreign Application Priority Data
Nov. 6, 2020  (EP) .................................. 20206226

(51) Int. Cl.
*C07C 7/14*  (2006.01)
*B01D 3/14*  (2006.01)
(Continued)

(52) U.S. Cl.
CPC ................ *C07C 7/14* (2013.01); *B01D 3/143* (2013.01); *B01D 3/40* (2013.01); *B01D 9/0013* (2013.01);
(Continued)

(58) Field of Classification Search
None
See application file for complete search history.

(56) References Cited

U.S. PATENT DOCUMENTS 5,817,865 A * 10/1998 Machhammer ......... C07C 51/43
  560/208
5,831,124 A * 11/1998 Machhammer ......... C07C 51/43
  562/600
(Continued)

FOREIGN PATENT DOCUMENTS

JP    61218535 A    9/1986

OTHER PUBLICATIONS

Lie-Ding Shiau; "Purification of Styrene from a Styrene/Ethylbenzene Mixture by Stripping Crystallization"; Industrial & Engineering Chemistry Research; c. 2018; vol. 57; pp. 6759-6765 (XP055775413).
(Continued)

*Primary Examiner* — Tam M Nguyen
(74) *Attorney, Agent, or Firm* — GLOBAL IP COUNSELORS, LLP

(57) ABSTRACT

A method for preparing a purified styrene composition is provided. The method includes providing a crude composi-
(Continued)

tion and subjecting the crude composition to at least one crystallization step. The crude composition contains 70% by weight or more styrene based on the total weight of the crude composition. The at least one crystallization step comprises at least one of a static crystallization stage and a dynamic crystallization stage. The crude composition contains at least one impurity selected from the group consisting of: color inducing species, oxygenates, sulfur species, alpha-methyl-styrene, and mixtures thereof.

12 Claims, 6 Drawing Sheets

(51) Int. Cl.
    *B01D 3/40*     (2006.01)
    *B01D 9/00*     (2006.01)
    *C07C 5/03*     (2006.01)
    *C07C 7/00*     (2006.01)
    *C07C 7/08*     (2006.01)

(52) U.S. Cl.
    CPC ......... *B01D 9/0031* (2013.01); *B01D 9/0059* (2013.01); *C07C 5/03* (2013.01); *C07C 7/005* (2013.01); *C07C 7/08* (2013.01); *B01D 2009/0086* (2013.01)

(56) References Cited

U.S. PATENT DOCUMENTS

| 5,849,982 | A | 12/1998 | Lee et al. | |
|---|---|---|---|---|
| 2013/0005925 | A1* | 1/2013 | Hutten | C07C 57/04 526/315 |
| 2017/0326471 | A1* | 11/2017 | Schäfer | C07C 51/43 |

OTHER PUBLICATIONS

European Search Report dated Feb. 22, 2021 in corresponding European Application No. 20206226.1.
International Search Report dated Jul. 14, 2021 in corresponding International Application No. PCT/EP2021/062208.

* cited by examiner

PROCESS AND APPARATUS FOR PREPARING PURIFIED STYRENE COMPOSITION FROM STYRENE CONTAINING FEEDSTOCK

CROSS-REFERENCE TO RELATED APPLICATION

This application is a U.S. National Stage application of International Application No. PCT/EP2021/062208, filed May 7, 2021, which claims priority to European Application No. 20206226.1, filed Nov. 6, 2020 and U.S. Provisional Application No. 63/022,109, filed May 8, 2020, the contents of each of which are hereby incorporated by reference.

FIELD OF THE INVENTION

The present disclosure relates to a method for preparing a purified styrene composition from a styrene containing feedstock, such as from naphtha cracked pyrolysis gasoline including specific impurities having melting points higher than styrene as well as optionally in addition thereto other impurities. Moreover, the present disclosure relates to a plant in which the method may be performed.

BACKGROUND OF THE INVENTION

Styrene is an important building block for polymers, such as polystyrene, acrylonitrile-butadiene-styrene (ABS)/styrene-acrylonitrile (SAN) resins, styrene-butadiene (SB) copolymer latexes, unsaturated polyester resins, styrene-butadiene rubber (SBR) elastomers and latexes. It is one of the highest volume commodity chemicals traded, and over 30% of annual styrene production is traded internationally. Predominantly, styrene is produced starting with raw materials benzene and ethylene. Benzene is alkylated to produce ethylbenzene (EB), and the EB is converted into styrene via the conventional dehydrogenation process or ethylbenzene/styrene monomer (EBSM) process, respectively, or the propylene oxide/styrene monomer (POSM) process. Typically, styrene plants are located near ethylene crackers due to the gaseous nature of ethylene which makes it relatively difficult to transport as compared to benzene.

Apart from the on-purpose production route via EBSM/POSM, styrene is also present in hydrocarbon streams, such as pyrolysis gasoline obtained from steam cracking of naphtha, hydrocarbon fraction obtained from polystyrene pyrolysis, gas oils etc. Styrene extraction from these hydrocarbon streams, although far less in quantity as compared to EBSM/POSM, presents an attractive economic opportunity to the operator due to the low feedstock cost. However, this separation is technically difficult due to the presence of close boiling molecules and impurities coming from the starting feedstock. Removal of close boiling molecules, such as mixed xylenes, ethylbenzene, etc., from styrene by normal distillation is an energy intensive process. Solvent based extractive distillation techniques, as advocated in U.S. Pat. No. 5,849,982, have been developed and commercially deployed which remove the close boiling molecules at reduced specific energy consumption.

Despite producing high purity styrene (>99.8 wt %), in general the extractive distillation route produces a styrene which contains, as compared to EBSM/POSM styrene, impurities such as chromophores, sulfur, oxygenates, etc. in the starting feedstock. These impurities affect the downstream polymerization process and, thereby, the properties of the polymer produced. Different methods for impurities removal have been cited based on chemical or adsorbent treatment. Chemical treatment may involve use of dienophiles, nitric acid, alkali, etc. Use of adsorbents may entail clays, alumina, etc. These additional treatment steps can produce a marketable product meeting the ASTM specification for styrene monomer. However, styrene losses via unwanted polymerization, and polymer formation across adsorbent beds due to the inherent heat sensitivity of styrene, require complex design precautions to prevent polymerization, and usage of complex equipment render these methods a nuisance for the owner/operator.

SUMMARY

Considering the above, the objective underlying the present disclosure is to provide a method for preparing a purified styrene composition from a styrene containing feed composition, such as in particular a styrene containing feed composition obtained by the extractive distillation route, such as from pygas from naphtha cracked pyrolysis gasoline or the like, which reliably and efficiently removes specific impurities resulting therefrom, such as color inducing species, sulfur species, alpha-methylstyrene and oxygenates, as well as in addition thereto other impurities, from the styrene in an energy efficient manner, even if the impurities are contained in a comparably high amount in the styrene containing feed composition, so as to obtain in a cost efficient manner a very pure styrene composition.

In accordance with the present disclosure, this object is satisfied by providing a method for preparing a purified styrene composition, the method comprising: providing a crude composition containing 70% by weight or more styrene based on a total weight of the crude composition, and subjecting the crude composition to at least one crystallization step, wherein: the at least one crystallization step comprises at least one of a static crystallization stage and a dynamic crystallization stage, and the crude composition contains at least one impurity selected from the group consisting of: color inducing species, oxygenates, sulfur species, alpha-methylstyrene, and mixtures thereof.

This solution is based on the surprising finding that by subjecting a crude styrene containing composition to a crystallization comprising at least one of a static crystallization stage and a dynamic crystallization stage, not only is a respective energy efficient method obtained, but in addition even impurities having a higher melting point than styrene, namely color inducing species, oxygenates, sulfur species, alpha-methylstyrene, such as they result from feed compositions obtained by the extractive distillation route, such as from pygas from naphtha cracked pyrolysis gasoline or the like, are reliably and completely, or at least substantially completely, removed from the styrene along with other impurities, such as those selected from the group consisting of: meta-xylenes, ortho-xylenes, ethylbenzene, phenylacetylene, cumene, n-propylbenzene, ethyltoluene, organo-chlorinated and organo-nitrogenated species, and mixtures thereof. This is surprising, since it is unexpected that some of these impurities having a higher melting point than styrene can be reliably and completely separated by crystallization from styrene. On the contrary, it must have been expected that such impurities cannot be separated by crystallization from styrene, because they have a higher melting point and thus are expected to crystallize before styrene. Therefore, even if it is known to purify certain styrene compositions, such as those comprising ethylbenzene, by crystallization, a person skilled in the art being confronted with the aforementioned object would have not considered to use crystallization for solving this object. Without wishing to be bound to any theory, the inventors of the present disclosure consider that the reason why styrene may be purified from the aforementioned impurities by crystallization is that the solubility of these impurities in the mother liquor is higher than the solubility in styrene crystals. This principle, in general, does not apply to any impurities contained in styrene. Thus, this surprising behavior applies specifically to the impurities as have been described above. This discovery enables removal of these impurities along with other impurities, such as those selected from the group consisting of: meta-xylenes, ortho-xylenes, ethylbenzene, phenylacetylene, cumene, n-propylbenzene, ethyltoluene, organo-chlorinated and organo-nitrogenated species, and mixtures thereof. As a result, the method in accordance with the present disclosure allows removal of the aforementioned impurities from styrene in a cost efficient manner. Therefore, the method in accordance with the present disclosure is particularly suitable for preparing a purified styrene composition from styrene containing compositions, which until now could not economically reasonably be used for the preparation of pure styrene, such as in particular from styrene containing compositions having been obtained by the extractive distillation route, such as from pygas from naphtha cracked pyrolysis gasoline or the like.

As set out above, the method in accordance with the present disclosure comprises the step of providing a crude composition containing styrene and subjecting the crude composition to at least one crystallization step. The step of providing a crude composition may comprise directly subjecting a styrene containing feed composition to the at least one crystallization step or first processing a styrene containing feed composition for instance by making use of one or more distillation steps or other steps, before the processed composition is subjected to the at least one crystallization step. In order to strictly divide between the respective styrene containing compositions, herein "crude composition containing styrene" or "crude composition" means the styrene containing composition that is subjected to the at least one crystallization step, whereas "styrene containing feed composition" means a composition from which the "crude composition containing styrene" may be prepared, and "purified styrene composition" means the styrene composition that is obtained after the crystallization.

Moreover, as conventionally known, crystallization processes or steps, respectively, may be carried out in multiple stages, i.e. in several crystallization stages. In view of this, in the present application a crystallization step is defined as comprising one or more crystallization stages.

As further set out above, the method in accordance with the present disclosure is particularly suitable for removing impurities having, at ambient pressure, a higher melting point than styrene. Accordingly, the crude composition preferably contains as impurities one or more impurities selected from the group consisting of: color inducing species, oxygenates, sulfur species, alpha-methylstyrene and mixtures thereof, each of the one or more impurities having a higher melting point than styrene. For instance, the melting point of the one or more above mentioned impurities is at ambient pressure −30° C. or more, such as −27° C. or more, −25° C., −20° C. or more or −15° C. or more. Suitable oxygenates, i.e. hydrocarbon compounds comprising at least one oxygen atom in the molecule, are water, alcohols, ketones, aldehydes and carboxylic acids. Color inducing species are defined as all compounds that impart color of more than 10 on a Pt-Co scale to styrene. Sulfur species are defined as all compounds containing at least one sulfur atom in the molecule.

In a further development of the idea of the present disclosure, it is proposed that the crude composition contains at least one of the following impurities:

one or more sulfur species selected from the group consisting of: alkyl, naphthenic or aromatic mercaptans, alkyl, naphthenic or aromatic disulfides, alkyl, aromatic, naphthenic or vinyl thiophenes (such as dimethyl thiophenes or vinyl thiophenes), oxygenated sulfur containing hydrocarbon compounds or any other hydrocarbon compound including at least one sulfur atom in its molecule and mixtures thereof, such as for instance sulfur species selected from the group consisting of mercaptans, disulfides, thiophenes having e.g. a boiling point of 130 to 150° C., and one or more color inducing species selected from the group consisting of: fulvenes, conjugated diolefins, oxygenated species, oxygenated sulfur species, styrene oligomers, alkynes and hydrocarbon compounds comprising conjugated olefin and alkyne bonds, and any other compound imparting a color of more than 10 as defined on Pt-Co scale to styrene, such as for instance selected from the group consisting of conjugated diolefins, oxygenated species and oxygenated sulfur species having e.g. a boiling point of 130 to 150° C.

Preferably, the crude composition used in the method in accordance with the present disclosure contains 10 to 30% by weight, and more preferably 10 to 20% by weight, based on the total weight of the crude composition, of one or more impurities selected from the group consisting of: color inducing species, oxygenates, sulfur species, alpha-methylstyrene, and mixtures thereof, and in particular one or more of the aforementioned impurities having a higher melting point (at ambient pressure) than styrene in the absence or in the presence of other impurities, such as those selected from the group consisting of: meta-xylenes, ortho-xylenes, ethylbenzene, phenylacetylene, cumene, n-propylbenzene, ethyltoluene, organo-chlorinated and organo-nitrogenated species and mixtures thereof. Surprisingly, even such high amounts of these impurities may be separated from styrene with the method in accordance with the present disclosure.

In addition to the aforementioned specific impurities, the crude composition used in the method in accordance with the present disclosure may contain one or more further impurities, such as one or more impurities selected from the group consisting of: meta-xylenes, ortho-xylenes, ethylbenzene, phenylacetylene, cumene, n-propylbenzene, ethyltoluene, organo-chlorinated and organo-nitrogenated species, and mixtures thereof.

In accordance with the present disclosure, the styrene content of the crude composition is at least 70% by weight. Preferably, the styrene content of the crude composition is more than 80 to 95% by weight, more preferably more than 95 to 99% by weight or more than 99% by weight, such as more than 99.8% by weight.

In accordance with the present disclosure, the at least one crystallization step comprises at least one of a static crystallization stage and a dynamic crystallization stage, i.e. i) at least one static crystallization stage, ii) at least one dynamic crystallization stage or iii) a combination of at least one static crystallization stage and at least one dynamic crystallization stage, so as to produce in the at least one crystallization step a styrene enriched crystallized fraction and a styrene depleted residue fraction.

In accordance with a preferred embodiment of the present disclosure, the crystallization is performed as melt crystallization. Therefore, it is preferred that the at least one static crystallization stage, if included, is at least one static melt crystallization stage and that the at least one dynamic crystallization stage, if included, is at least one dynamic melt crystallization stage.

Good results are particularly obtained when as at least one dynamic crystallization stage, a falling film crystallization stage, and more preferably a falling film melt crystallization stage, is used. Alternatively, preferably as at least one dynamic crystallization stage, a suspension crystallization stage, and more preferably a suspension melt crystallization stage, is used.

In particular, the present disclosure does not comprise any crystallization stage making use of a high pressure inert light gas to create chilling via a Joule Thomson effect. Therefore, none of the at least one crystallization step of the method in accordance with the present disclosure comprises admixing to the crude composition a liquefied normally gaseous hydrocarbon while maintaining a temperature and pressure on the mixture such as to cause at least the major portion of the liquefied normally gaseous hydrocarbon to remain in liquid phase, introducing the resulting mixture into a pressure reduction zone and reducing the pressure on the mixture thereby causing evaporation of at least a portion of the liquefied normally gaseous hydrocarbon with consequent chilling of the remaining mixture being sufficient to cause the formation of styrene crystals but insufficient of causing the formation of solid eutectic.

Preferably, the at least one crystallization step of the method comprises at least one static melt crystallization stage, at least one falling film melt crystallization stage, at least one suspension melt crystallization stage, or a combination of two or more thereof.

In accordance with a preferred embodiment of the present disclosure, the at least one crystallization step of the method comprises at least one of a static melt crystallization stage and at least one dynamic melt crystallization stage. By using static crystallization and dynamic crystallization, the disadvantages of both technologies are minimized by the combination, namely the slowness of static crystallization by also using the much faster dynamic crystallization, and the energy intensity of dynamic crystallization by also using the much more energy efficient static crystallization.

For instance, the at least one crystallization step comprises i) at least one static crystallization stage, and ii) at least one of, at least one falling film crystallization stage and at least one suspension crystallization stage.

In a further development of the idea of the present disclosure, it is suggested that the method comprises a crystallization step, which comprises one to ten static crystallization stages and one to ten dynamic crystallization stages. Even more preferably, the method comprises a crystallization step that includes one to five static crystallization stages and one to five dynamic crystallization stages. If the method comprises two or more dynamic crystallization stages and/or two or more static crystallization stages, each of the dynamic crystallization stages is fluidly coupled with one or two other dynamic crystallization stages, each of the static crystallization stages is fluidly coupled with one or two other static crystallization stages, and one of the dynamic crystallization stages is fluidly coupled with one of the static crystallization stages. In other words, the dynamic crystallization stages are arranged in series with each other and the static crystallization stages are arranged in series with each other. The numbering starts from the static crystallization stage and the dynamic crystallization stage, which are fluidly coupled together. Thus, if the crystallization comprises four dynamic crystallization stages and four static crystallization stages, the first dynamic crystallization stage and the first static crystallization stage are those which are coupled with each other. The first dynamic crystallization stage is fluidly coupled with the second dynamic crystallization stage, which is also coupled with the third dynamic crystallization stage, wherein the third dynamic crystallization stage is also coupled with the fourth dynamic crystallization stage. Likewise thereto, the first static crystallization stage is fluidly coupled with the second static crystallization stage, which is also coupled with the third static crystallization stage, wherein the third static crystallization stage is also coupled with the fourth static crystallization stage. In both series, the first crystallization stage is the most upstream crystallization stage, wherein the second, third and fourth crystallization stages are located downstream of the first crystallization stage.

In accordance with a first preferred embodiment of the present disclosure, the method comprises a crystallization step that includes one static crystallization stage and one dynamic crystallization stage. In this variant, the crude composition is preferably fed into the dynamic crystallization stage so as to produce a styrene enriched crystallized fraction and a styrene depleted residue fraction. The styrene depleted residue fraction obtained in the dynamic crystallization stage mainly contains the styrene depleted mother liquor and is fed into the static crystallization stage as feed. Also in the static crystallization stage, a styrene enriched crystallized fraction and a styrene depleted residue fraction are produced, wherein the styrene enriched crystallized fraction obtained in the static crystallization stage is fed into the dynamic crystallization stage and mixed there with the crude composition fed into the dynamic crystallization stage. The styrene depleted residue fraction obtained in the static crystallization stage is withdrawn, whereas the styrene enriched crystallized fraction obtained in the dynamic crystallization stage is withdrawn as the purified styrene composition. In principle, as an alternative to the above description, the crude composition may be fed into the static crystallization stage, i.e. the static crystallization and dynamic crystallization stages may be arranged in reversed order to the aforementioned description. However, better results are obtained when the crude composition is fed into the dynamic crystallization stage. For the sake of completeness, it is noted that the aforementioned terms "styrene enriched crystallized fraction" and "styrene depleted residue fraction" are meant relative to the styrene content of the input into the respective crystallization stage and not relative to the styrene content of the crude composition. In other words, the styrene enriched crystallized fraction obtained in the static crystallization stage has a higher styrene content than the input into this static crystallization stage (which is the styrene depleted residue fraction fed from the dynamic crystallization stage into the static crystallization stage) and the styrene depleted residue fraction has a lower styrene content than the input into this static crystallization stage.

In accordance with a second preferred embodiment of the present disclosure, the method comprises a crystallization step that includes two to five static crystallization stages and two to five dynamic crystallization stages. Preferably, the crude composition is fed into the first of the two to five dynamic crystallization stages so as to produce a first styrene enriched crystallized fraction and a first styrene depleted residue fraction, wherein the first styrene enriched crystallized fraction is fed into the second of the two to five dynamic crystallization stages, wherein in any of the second and of the optional third to fifth dynamic crystallization stages, a styrene enriched crystallized fraction and a styrene depleted residue fraction is produced, wherein each of the styrene enriched crystallized fractions produced in the second and the optional third to fourth dynamic crystallization stages is fed into a downstream dynamic crystallization stage, and each of the styrene depleted residue fractions produced in the second and the optional third to fifth dynamic crystallization stages is fed into an upstream dynamic crystallization stage. The first styrene depleted residue fraction is fed into the first of the two to five static crystallization stages so as to produce a second styrene enriched crystallized fraction and a second styrene depleted residue fraction, wherein the second styrene enriched crystallized fraction is fed into the first dynamic crystallization stage, and the second styrene depleted residue fraction is fed into the second of the two to five static crystallization stages. In any of the second and of the optional third to fifth static crystallization stages, a styrene enriched crystallized fraction and a styrene depleted residue fraction is produced, wherein each of the styrene depleted residue fractions produced in the second and the optional third to fourth static crystallization stages is fed into a downstream static crystallization stage and each of the styrene enriched crystallized fractions produced in the second and the optional third to fifth dynamic static stages is fed into an upstream static crystallization stage. In principle, the crude composition may be fed into one of the static crystallization stages, i.e. the static crystallization and dynamic crystallization stages may be arranged in reversed order to the aforementioned description. However, better results are obtained when the crude composition is fed into one of the dynamic crystallization stage.

In an alternative embodiment, the crude composition is fed into the second of the two to five dynamic crystallization stages and not into the first dynamic crystallization stage, wherein first to fifth is again seen in the direction upstream to downstream. Again, the most upstream dynamic crystallization stage (i.e. the first dynamic crystallization stage) is that which receives a styrene enriched crystallized fraction from the first static crystallization stage and from which a styrene depleted residue fraction is fed into the first static crystallization stage, whereas the most downstream dynamic crystallization stage is that from which the purified styrene composition is withdrawn. Likewise, the most upstream static crystallization stage (i.e. the first static crystallization stage) is that which receives a styrene depleted residue fraction from the first dynamic crystallization stage and from which a styrene enriched crystallized fraction is fed into the first dynamic crystallization stage, whereas the most downstream static crystallization stage (i.e. the second static crystallization stage) is that from which the styrene depleted residue fraction is withdrawn.

For instance, the method comprises a crystallization step that includes two static crystallization stages and four dynamic crystallization stages. In this embodiment, the crude composition is fed into the second of the dynamic crystallization stages so as to produce a second styrene enriched crystallized fraction and a second styrene depleted residue fraction. The second styrene enriched crystallized fraction is fed into the third of the four dynamic crystallization stages so as to produce a third styrene enriched crystallized fraction and a third styrene depleted residue fraction, wherein the third styrene enriched crystallized fraction is fed into the fourth of the dynamic crystallization stages so as to produce a fourth styrene enriched crystallized fraction and a fourth styrene depleted residue fraction. While the fourth styrene enriched crystallized fraction is withdrawn as purified styrene composition, the fourth styrene depleted residue fraction is fed into the third dynamic crystallization stage, the third styrene depleted residue fraction is fed into the second dynamic crystallization stage, and the second styrene depleted residue fraction is fed into the first dynamic crystallization stage. In the first dynamic crystallization stage, a first styrene enriched crystallized fraction and a first styrene depleted residue fraction are produced. While the first styrene enriched crystallized fraction is fed into the second dynamic crystallization stage, the first styrene depleted residue fraction is fed into the first of the two static crystallization stages, in which a fifth styrene enriched crystallized fraction and a fifth styrene depleted residue fraction are produced. While the fifth styrene enriched crystallized fraction is fed into the first dynamic crystallization stage, the fifth styrene depleted residue fraction is fed into the second of the two static crystallization stages, in which a sixth styrene enriched crystallized fraction and a sixth styrene depleted residue fraction are produced. While the sixth styrene enriched crystallized fraction is fed into the first static crystallization stage, the sixth styrene depleted residue fraction is removed.

In all of the above described methods, preferably the production of a styrene enriched crystallized fraction and of a styrene depleted residue fraction in a crystallization stage comprises the steps of: (1) removing the remaining liquid from the crystallization stage as styrene depleted residue fraction after termination of the crystallization in the crystallization stage, (2) melting the crystal layer obtained in the crystallization stage, and (3) withdrawing the obtained crystal melt as styrene enriched crystallized fraction from the crystallization stage.

In order to increase the purity of the purified styrene product, it is preferable to perform in any static and falling film crystallization stages, if present, at least one sweating step before melting the crystal layers formed on the cooled surfaces of the crystallizer used in the single crystallization stages. Sweating means that the crystal layers deposited on the cooled surfaces are gently heated to a temperature close to the melting temperature of styrene in order to partially melt the crystals. Trapped and adherent melt, which contains the impurities, drains off during the partial melting of the crystals and is then removed from the crystallizer. In order to conduct such a sweating, the surface, on which the crystals are deposited, is heated with a heat transfer medium to the desired temperature. The sweating may be performed for one or several times before melting the crystal layers deposited on the cooled surfaces. Thus, the sweating leads to one or more sweating fractions and a purified crystal layer. Preferably, at least a portion of the first sweating fraction obtained thereby is fed to the remaining liquid which has been removed as styrene depleted residue fraction.

The crystallization temperature depends on the composition of the crude composition. However, good results are obtained when at least one and preferably all of the at least one static melt crystallization stage and the at least one dynamic melt crystallization stage are performed at a temperature of −200° C. and 30° C. and more preferably at a temperature of −140° C. and 0° C. In the case of static crystallization comprising one or more sweating steps and in the case of falling film crystallization comprising one or more sweating steps, at least one and preferably all of the crystallization stages may be performed at a temperature of −100° C. and −30° C.

Depending on the composition of the feed composition, the feed composition may be directly fed as crude composition to the at least one crystallization step or may be first processed with another technique, before the processed feed composition is fed as crude composition to the at least one crystallization step. For example, the step of providing the crude composition comprises subjecting a feed composition to one or more distillation steps and/or one or more extractive distillation steps, wherein the crude composition is obtained as a head stream, as a side stream or as a bottom stream of one of the at least one of the one or more distillation steps and one or more extractive distillation steps.

Preferably, the feed composition is subjected to one or more extractive distillation steps using a polar solvent. Suitable polar solvents are solvents selected from the group consisting of: propylene carbonate, sulfolane, tetramethyl sulfolane, methyl carbitol, 1-methyl-2-pyrrolidinone, 2-pyrrolidinone and mixtures of the aforementioned solvents, but not including water. The extractive solvent may be also a two-part extractive solvent with one part being a solvent from the aforementioned group and the second part being water, wherein both parts of the extractive solvent are fed into the distillation column separately and independently from each other at different locations along the distillation column.

As set out above, the method in accordance with the present disclosure is particularly suitable for preparing a purified styrene composition from styrene containing compositions, which until now could not economically reasonably be used for the preparation of pure styrene. Therefore, it is preferred that the crude composition derives from a pygas. The method of the present disclosure allows for cost efficient purification of styrene from such feed compositions, which is not possible with conventional methods. In particular, the crude composition may originate from an extractive distillation process employed on naphtha cracker pyrolysis gasoline. These pygases are known to contain impurities, such as color inducing species. $C_6$-thiophenic sulfur species and oxygenates originating from pygas feed as well as air leaks in the vacuum equipment used in the process. Moreover, they contain impurities having a boiling point close to that of styrene, such as ortho-xylene, which are difficult to remove completely via extractive distillation. It is preferred in this embodiment that the crude composition is/has been prepared by distilling a pygas feed composition so as to obtain a $C_8$-fraction and subjecting the $C_8$-fraction to an extractive distillation, in which the $C_8$-fraction is treated with a polar solvent so as to obtain a styrene containing fraction as an overhead stream, as a side stream or as a bottom stream. The so-obtained styrene containing fraction may be processed into the crude composition, for instance by means of a distillation step, or, preferably, the so-obtained styrene containing fraction is used as the crude composition which is fed to the crystallization step.

In an alternative embodiment of the present disclosure, the crude composition is/has been prepared by distilling a pygas feed composition so as to obtain a $C_8$-fraction, feeding the $C_8$-fraction into a hydrogenation reactor, in order to hydrogenate for instance phenylacetylene so as to obtain a hydrogenated gas, and subjecting the hydrogenated gas to an extractive distillation, in which the hydrogenated gas is treated with a polar solvent so as to obtain a styrene containing fraction as an overhead stream, as a side stream or as a bottom stream. The so-obtained styrene containing fraction may be processed into the crude composition, for instance by means of a distillation step, or, preferably, the so-obtained styrene containing fraction is used as the crude composition which is fed to the crystallization step.

Preferably, the hydrogenation is performed so that, while phenylacetylene is hydrogenated, the styrene loss is less than 0.1% by weight.

In order to recover the solvent used in the extractive distillation, it is preferred that the styrene containing fraction is subjected to a distillation step so as to remove at least a portion of the polar solvent from the styrene containing fraction, thereby obtaining the crude composition.

The method in accordance with the present disclosure results in a very pure styrene containing composition. Preferably, the purified styrene composition has a styrene content of at least 99.00% by weight, more preferably of at least 99.50% by weight, even more preferably of at least 99.80% by weight, still more preferably of at least 99.90% by weight, yet more preferably of at least 99.95% by weight and most preferably of at least 99.98% by weight.

In particular, the method in accordance with the present disclosure allows for the complete or at least nearly complete removal of color inducing species from the crude styrene containing composition. Therefore, in a further development of the idea of the present disclosure, it is proposed that the purified styrene composition has a color of maximum 15 as defined by Pt-Co scale as per ASTM D5386.

Furthermore, the method in accordance with the present disclosure allows for the complete or at least nearly complete removal of sulfur species from the crude styrene containing composition. Consequently, it is particularly preferred that the purified styrene composition comprises less than 5 ppmw, more preferably less than 4 ppmw, even more preferably less than 3 ppmw and most preferably less than 2 ppmw, of total elemental sulfur as contained in mercaptans, disulfides and thiophenes and/or less than 20 ppmw of oxygenates.

In addition, the method in accordance with the present disclosure allows one to obtain a purified styrene composition, which comprises less than 40 ppmw of impurities selected from the group consisting of: phenylacetylene, mixed xylenes, ethylbenzene, cumene, ethyltoluene, n-propylbenzene, and alpha-methylstyrene, and/or which has polymer content of less than 10 ppmw.

Preferably, the purified styrene composition has total organic chlorine content of less than 2 ppmw.

For instance, the purified styrene composition may meets the following specifications.

TABLE 1

| Parameter | Unit | Specification | Test Method |
| --- | --- | --- | --- |
| Color | Pt/Co scale | 15 max. | ASTM D5386 |
| Styrene monomer purity | Wt % | 99.8 min. | ASTM D5135 or 7504 |
| Aldehydes as benzaldehyde | Wt ppm | 75 max. | ASTM D2119 |
| Peroxides as $H_2O_2$ | Wt ppm | 15 max. | ASTM D2340 |
| Polymer content | Wt ppm | 10 max. | ASTM D2121 Test Method A |
| Inhibitor (tert-butylcatechol) | Wt ppm | 10 max. | ASTM D4590 |
| Ethylbenzene | Wt ppm | 500 max. | ASTM D5135 or D7504 |
| Benzene | Wt ppm | 1 max. | ASTM D6229 |
| Phenylacetylene | Wt ppm | 150 max. | ASTM D5135 |
| Water | Wt ppm | 50 max. | ASTM E1064 |
| Total organic Chlorides | Wt ppm | 2 max. | ASTM D5808 |
| Copper and Manganese | Wt ppm | 5 max. | UOP 389 or 407 |

TABLE 1-continued

| Parameter | Unit | Specification | Test Method |
| --- | --- | --- | --- |
| Viscosity at 25° C. | cP | 0.75 max. | |
| Appearance | — | Clear, transparent liquid free of sediment and haze at 18 to 25° C. | |

The residual mother liquor, i.e. the styrene depleted residue fraction obtained in the crystallization, is discharged. Preferably, none of the styrene depleted residue fraction obtained in the crystallization is recycled in the method to an optional distillation step and, if so, at most 50% by volume, more preferably at most 20% by volume, and yet more preferably at most 10% by volume, is recycled.

According to a further aspect, the present disclosure relates to a plant for preparing a purified styrene composition comprising: at least one crystallization block, the at least one crystallization block comprising: at least one of a static crystallization section comprising one or more static crystallization stages and a dynamic crystallization section comprising one or more dynamic crystallization stages; and at least one extractive distillation column comprising two or more outlets, wherein at least one of the two or more outlets is fluidly coupled with an inlet of the crystallization block.

The term "crystallization block" refers to an apparatus for a purification process with one or more crystallizers. Moreover, the term "crystallization stage" is not only used to denote a method step or stage, respectively, but also to denote an apparatus, namely that part of a crystallizer in which a crystallization stage is performed. The crystallization stage as an apparatus feature may be also designated as crystallizer, crystallizer unit or the like.

Preferably, the plant further comprises a solvent recovery distillation column, which is fluidly coupled with an outlet of the extractive distillation column.

Good results are in particular obtained, when the crystallization block of the plant comprises:

at least one static crystallization section comprising one or more static crystallization stages, at least one dynamic crystallization section comprising one or more dynamic crystallization stages and at least two conduits that fluidly couple at least one of the one or more static crystallization stages with at least one of the one or more dynamic crystallization stages.

Preferably, the one or more static crystallization stages are static melt crystallization stages and the one or more dynamic crystallization stages are dynamic melt crystallization stages.

If the crystallization block comprises two or more dynamic crystallization stages and/or two or more static crystallization stages, preferably each of the dynamic crystallization stages is fluidly coupled with one or two other dynamic crystallization stages and each of the static crystallization stages is fluidly coupled with one or two other static crystallization stages.

Moreover, it is preferred that the at least one crystallization block comprises one static crystallization stage and one dynamic crystallization stage, wherein one of the at least two conduits fluidly couples the static crystallization stage with the dynamic crystallization stage so that a styrene depleted residue fraction obtained in the dynamic crystallization stage may be fed into the static crystallization stage, and wherein one other of the at least two conduits fluidly couples the static crystallization stage with the dynamic crystallization stage so that a styrene enriched crystallized fraction obtained in the static crystallization stage may be fed into the dynamic crystallization stage.

Moreover, it is preferred that the at least one crystallization block comprises two to five static crystallization stages and two to five dynamic crystallization stages, wherein one of the at least two conduits fluidly couples one of the static crystallization stages with one of the dynamic crystallization stages so that a styrene depleted residue fraction obtained in the dynamic crystallization stage may be fed into the static crystallization stage fluidly coupled with the dynamic crystallization stage, and wherein one of the at least two conduits fluidly couples the static crystallization stage with the dynamic crystallization stage fluidly coupled with the static crystallization stage so that a styrene enriched crystallized fraction obtained in the static crystallization stage may be fed into the dynamic crystallization stage, wherein each two of the remaining static crystallization stages are fluidly coupled with each other by means of at least two conduits, and wherein each two of the remaining dynamic crystallization stages are fluidly coupled with each other by means of at least two conduits.

In accordance with a further preferred embodiment of the present disclosure, the plant comprises the at least one crystallization block, a distillation column and the at least one extractive distillation column, wherein the distillation column is fluidly coupled with the extractive distillation column via a conduit and wherein the extractive distillation column is fluidly coupled with the inlet of the crystallization block via an inlet conduit. Preferably, the plant of this embodiment further comprises a hydrogenation reactor and a further distillation column for solvent recovery, wherein the distillation column is fluidly coupled with the hydrogenation reactor via a conduit, wherein the hydrogenation reactor is fluidly coupled with the extractive distillation column via a conduit, wherein the extractive distillation column is fluidly coupled with the further distillation column for solvent recovery via a conduit, and wherein the further distillation column is fluidly coupled with the crystallization block via the inlet conduit.

In accordance with an alternative preferred embodiment of the present disclosure, the plant comprises the at least one crystallization block and three distillation columns, wherein the three distillation columns are fluidly coupled with each other and are arranged in series, wherein the last of the three distillation columns is fluidly coupled with the crystallization block via an inlet conduit. Preferably, the plant of this embodiment further comprises an alkylation unit and a dehydrogenation unit, wherein the alkylation unit is fluidly coupled with the dehydrogenation unit via a conduit and the dehydrogenation unit is fluidly coupled with the crystallization block via the inlet conduit.

The crystallization block comprises a product outlet line for discharging the purified styrene composition and a discharge line for discharging the residual mother liquor, i.e. the styrene depleted residue fraction obtained in the crystallization. Preferably, the plant does not comprise a recirculation line leading from the discharge line for discharging the styrene depleted residue fraction obtained in the crystallization to any of the distillation column(s).

In accordance with still an alternative preferred embodiment of the present disclosure, the plant further comprises a pyrolysis reactor, wherein the pyrolysis reactor is fluidly coupled with the at least one extractive distillation column.

BRIEF DESCRIPTION OF THE DRAWINGS

The disclosure will be explained in more detail hereinafter with reference to the drawings.

DETAILED DESCRIPTION

Figure 1A:
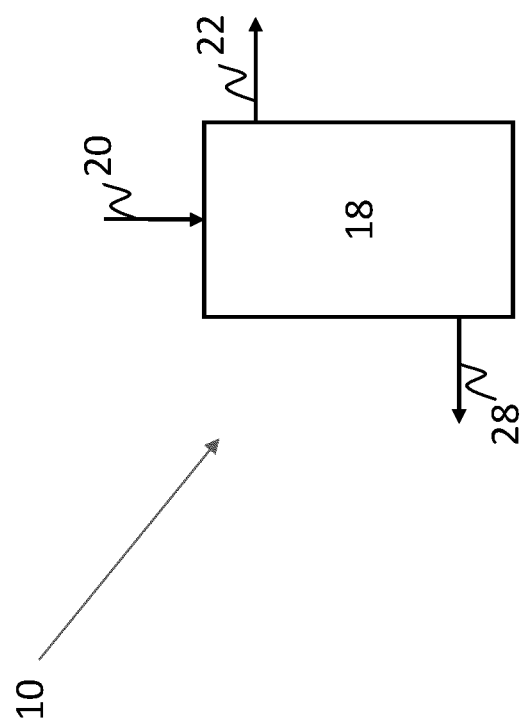
FIG. 1a is a diagrammatic illustration of a crystal block used in a method and plant in accordance with one embodiment of the present disclosure.

FIG. 1a shows an embodiment of a crystallization block 10 for conducting the process for preparing a purified styrene composition in accordance with an embodiment of the present disclosure. The crystallization block 10 includes a static melt crystallization stage 18 or one static melt crystallizer, respectively. The static melt crystallizer 18 is connected with an inlet conduit 20 for crude styrene containing composition which is suitable for feeding a crude styrene composition into the static melt crystallizer 18. In addition, the static melt crystallizer 18 has a discharge conduit 22 for the discharge of a purified styrene composition from the static melt crystallizer 18 and from the crystallization block 10. Moreover, the static melt crystallizer 18 comprises a discharge conduit 28 which serves for discharging a styrene depleted residue fraction, which is obtained by the crystallization in the static melt crystallizer 18, from the static melt crystallizer 18 and from the crystallization block 10.

Figure 1B:
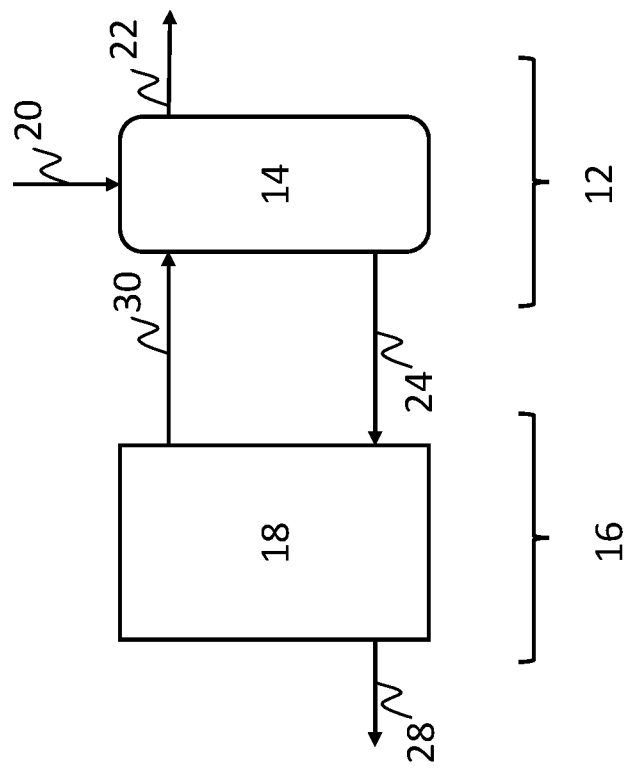
FIG. 1b is a diagrammatic illustration of a crystal block used in a method and plant in accordance with another embodiment of the present disclosure.

FIG. 1b shows another embodiment of a crystallization block 10 for conducting the process for preparing a purified styrene composition in accordance with an embodiment of the present disclosure. The crystallization block 10 includes a first dynamic melt crystallization section 12 which comprises one falling film crystallization stage or one falling film crystallizer 14, respectively as a dynamic melt crystallization stage or crystallizer, respectively. In addition, the crystallization block 10 comprises a second static melt crystallization section 16 having one static melt crystallization stage 18 or one static melt crystallizer, respectively. The falling film crystallizer 14 is connected with an inlet conduit 20 for crude styrene containing composition which is suitable for feeding a crude styrene composition into the falling film crystallizer 14. In addition, the falling film crystallizer 14 has a discharge conduit 22 for the discharge of a purified styrene composition from the falling film crystallizer 14 and from the crystallization block 10. The static melt crystallizer 18 is connected with the falling film crystallizer 14 via a transfer conduit 24 which is suitable for transferring a first styrene depleted residue fraction obtained by crystallization in the falling film crystallizer 14 into the static melt crystallizer 18. In this respect, the transfer conduit 24 is in fluid communication with both the falling film crystallizer 14 and the static melt crystallizer 18. The static melt crystallizer 18 comprises a discharge conduit 28 which serves for discharging a second styrene depleted residue fraction, which is obtained by the crystallization in the static melt crystallizer 18, from the static melt crystallizer 18 and from the crystallization block 10. A recycle conduit 30 provides a fluid communication between the static melt crystallizer 18 and the falling film crystallizer 14 and therefore allows for recycling of at least a part of the second styrene enriched crystallization composition, which results from the crystallization in the static melt crystallizer 18, back into the falling film crystallizer 14.

Figure 1C:
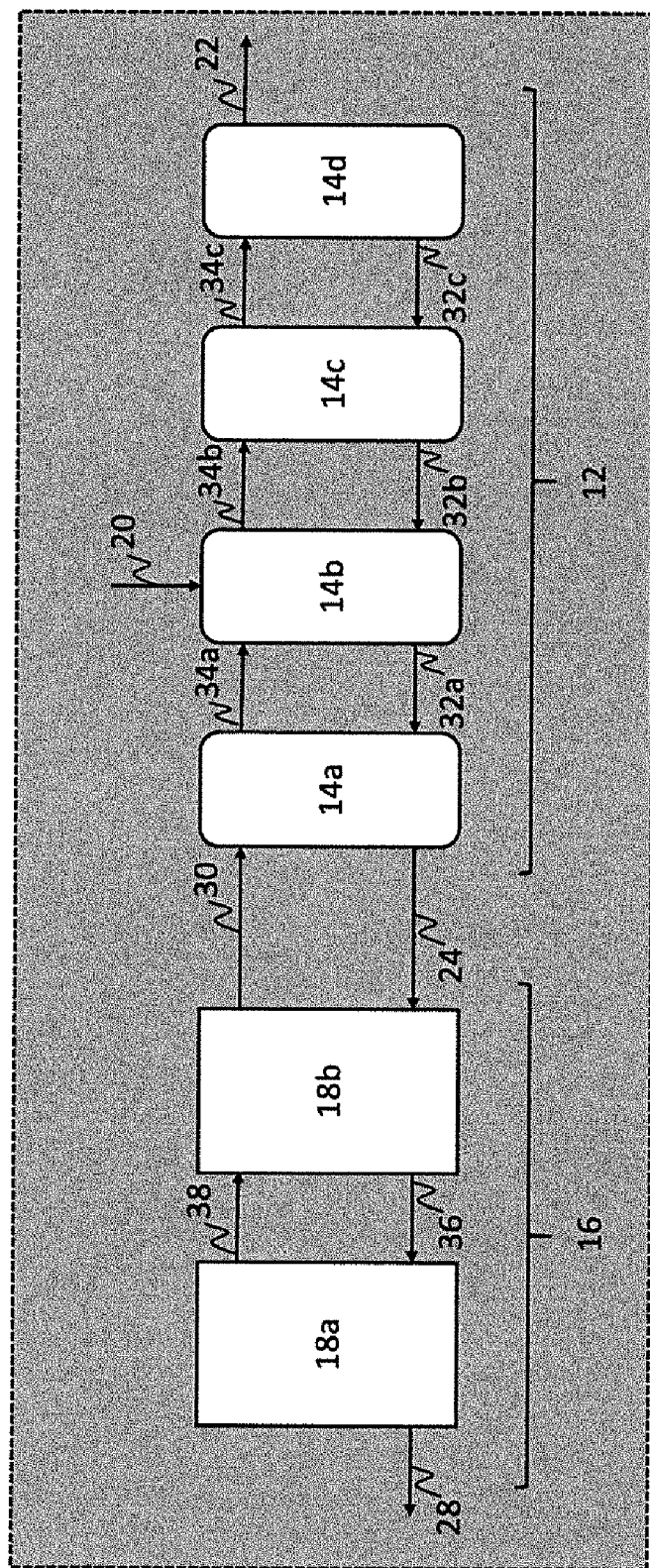
FIG. 1c is a diagrammatic illustration of a crystal block used in a method and plant in accordance with an embodiment of the present disclosure.

In FIG. 1c, another embodiment of a crystallization block 10 for conducting the method for preparing a purified styrene composition in accordance with the present disclosure is shown. The first dynamic melt crystallization section 12 comprises four falling film crystallization stages 14a, 14b, 14c, 14d and the second static melt crystallization section 16 includes two static melt crystallization stages 18a, 18b. There are provided transfer conduits 32a, 32b, 32c between the falling film crystallization stages 14a, 14b, 14c, 14d, through which a styrene depleted residue fraction obtained by falling film crystallization in the single falling film crystallization stages 14a, 14b, 14c, 14d can be transferred from one of the falling film crystallization stages 14b, 14c, 14d to the respective upstream falling film crystallization stages 14a, 14b, 14c. In addition, the falling film crystallization stages 14a, 14b, 14c, 14d are connected via recycle conduits 34a, 34b, 34c suitable for recycling at least a part of the styrene enriched crystallized fractions obtained by falling film crystallization in the single falling film crystallization stages 14a, 14b, 14c. 14d from one of the falling film crystallization stages 14a, 14b, 14c to the respective downstream falling film crystallization stages 14b, 14c, 14d. An inlet conduit 20 is connected to the second falling film crystallization stage 14b such that a crude styrene containing composition can be introduced into the second falling film crystallization stage 14b. A discharge conduit 22 is provided at the most downstream falling film crystallization stage 14d in order to remove the purified styrene composition from the crystallization block 10. A transfer conduit 24 provides a fluid communication between the most upstream falling film crystallization stage 14a of the first dynamic melt crystallization section 12 and the most upstream static melt crystallization stage 18b of the second static melt crystallization section 16 so that the styrene depleted residue fraction obtained by the crystallization in the falling film crystallization stage 14a can be transferred into the static crystallizer 18b of the second static melt crystallization section 16. The static melt crystallization stages 18a and 18b are connected via a transfer conduit 36 for transferring the styrene depleted residue fraction obtained by crystallization from the static melt crystallization stage 18b to the static melt crystallization stage 18a. In addition, the static melt crystallization stage 18a and the static melt crystallization stage 18b are connected via a recycle conduit 38 allowing for transferring the styrene enriched crystallized fraction, which results from the crystallization in the static melt crystallization stage 18a, into the static melt crystallizer of the crystallization stage 18b. Furthermore, the static melt crystallization stage 18a comprises a discharge conduit 28 for discharging the styrene depleted residue fraction, which is obtained by crystallization in the static melt crystallization stage 18a, from the crystallization block 10. A recycle conduit 30 provides a fluid communication between the static melt crystallization stage 18b and the falling film crystallization stage 14a and therefore allows for recycling of at least a part of the styrene enriched crystallized fraction obtained in the static melt crystallization stage 18b of the second static melt crystallization section 16 back into the falling film crystallization stage 14a of the first dynamic melt crystallization section 12.

During operation of the apparatus 10 shown in FIG. 1c, a crude styrene containing composition is fed into the falling film crystallization stage 14b via the inlet conduit 20. In each of the falling film crystallization stages 14a. 14b, 14c, 14d a styrene enriched crystallized composition and a styrene depleted residue fraction are prepared. Each of the styrene depleted residue fractions obtained in one of the falling film crystallization stages 14b, 14c, 14d is transferred via the transfer conduits 32a, 32b. 32c to the respective upstream falling film crystallization stage 14a, 14b, 14c. In addition, each of the styrene enriched fractions obtained in one of the falling film crystallization stages 14a, 14b, 14c is at least partially recycled via the recycle conduits 34a, 34b, 34c to the respective downstream falling film crystallization stage 14b, 14c, 14d. The styrene depleted residue fraction obtained after the crystallization in the falling film crystallization stage 14a of the first dynamic melt crystallization section 12 is transferred via the transfer conduit 24 into the static melt crystallization stage 18b of the second static melt crystallization section 16. The styrene depleted residue fraction obtained in the static melt crystallization stage 18b is transferred via the transfer conduit 36 to the downstream static melt crystallization stage 18a. In addition, the styrene enriched crystallized fraction obtained in the static melt crystallization stage 18a is at least partially recycled via the recycle conduit 38 into the upstream static melt crystallization stage 18b. The styrene enriched crystallized fraction obtained after the crystallization in the static melt crystallization stage 18b is recycled via the recycle conduit 30 into the falling film crystallization stage 14a of the first dynamic melt crystallization section 12. A finally purified styrene composition obtained in the crystallization stage 14d is removed from the apparatus 10 via the discharge conduit 22, while the final styrene depleted residue fraction is removed from the static melt crystallization stage 18a and from the apparatus 10 via the discharge conduit 28.

In accordance with the present disclosure) Table 2 lists the different impurities that can be typically present in a crude styrene stream along with their melting points. The reason for impurities removal from crude styrene stream by crystallization block is twofold a) Some of the species have melting points lower than styrene and b) during the crystallization process, impurities which have higher melting point are more soluble in the mother liquor. Thus, despite having a higher melting point, these impurities can be removed from styrene by crystallization. Thus, crystallization offers a unique method of producing highly purified styrene compositions, as desired by operator, from a crude styrene containing composition. Increasing product purity is directly correlated with an increasing number of crystallization stages. Recovery, on the other hand, is a function of the number of residue stages.

TABLE 2

| COMPOUND | MELTING POINT | |
| --- | --- | --- |
| Water | 0° C. | (32° F.; 273 K) |
| α-Methylstyrene | −23° C. | (−9.4° F.; 250 K) |
| o-Xylene | −25.2° C. | (−13.4° F.; 248 K) |
| Benzaldehyde | −26° C. | (−14.8° F.; 247 K) |
| Styrene | −30.6° C. | (−23.1° F.; 243 K) |
| Thiophenic compounds boiling in the range 130-150° C. | −65 to −30° C. | (−85 to −22° F.; 208 to 243 K) |
| Phenylacetylene | −45° C. | (−49° F.; 228 K) |
| Ethylbenzene | −95° C. | (−139° F.; 178 K) |

TABLE 2-continued

| COMPOUND | MELTING POINT | |
| --- | --- | --- |
| 3-Ethyltoluene (m-ethyltoluene) | −95.5° C. | (−140° F.; 177.6 K) |
| Cumene | −96° C. | (−141° F.; 177 K) |
| n-Propylbenzene | −99.5° C. | (−147° F.; 173.7 K) |

Figure 2:
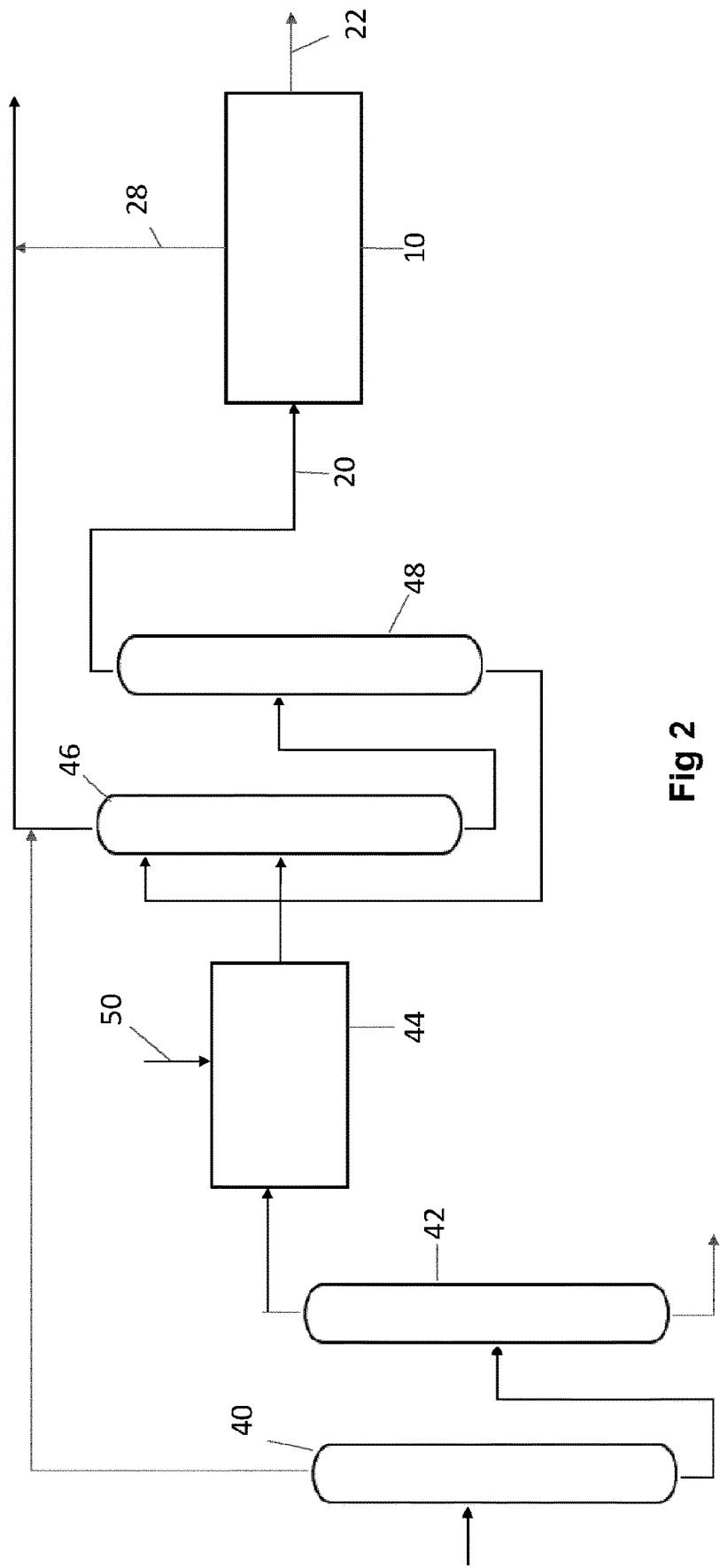
FIG. 2 is a diagrammatic illustration of a plant particularly suitable for purifying naphtha cracked pyrolysis gasoline in accordance with another embodiment of the present disclosure.

FIG. 2 shows schematically a plant particularly suitable for preparing a purified styrene composition from naphtha cracker pyrolysis gasoline. The plant 11 comprises a first distillation column 40, a second distillation column 42, a hydrogenation reactor 44, an extractive distillation column 46, a solvent recovery distillation column 48 and a crystallization block 10. The crystallization block 10 is composed as that shown in FIG. 1a, as that shown in FIG. 1b or as that shown in FIG. 1c.

During the operation of the plant, a $C_{7+}$-pygas stream is distilled in the first distillation column 40 and the bottom stream obtained in the first distillation column 40 is fed to the second distillation column 42 so as to obtain a $C_{9+}$-stream as bottom product and a $C_8$-rich stream as overhead product. The so-obtained $C_8$-rich stream is fed into the hydrogenation reactor 44 in order to hydrogenate phenyl acetylene included in the stream by hydrogen, which is supplied into the hydrogenation reactor 44 via the hydrogen inlet conduit 50. The hydrogenation reactor 44 is operated under mild conditions in order to saturate phenylacetylene to produce styrene; however, this is accompanied by styrene loss in the form of saturation which produces ethylbenzene. Post hydrogenation, the hydrogenated $C_8$-stream obtained in the hydrogenation reactor 44, consisting primarily of ethylbenzene, mixed xylenes etc., is fed into the extractive distillation setup comprising the extractive distillation column 46 and the solvent recovery distillation column 48. A polar solvent is used during the extractive distillation so as to extract a styrene and solvent containing stream as a bottom stream, which is then fed into the solvent recovery distillation column 48 so as to remove the solvent and to obtain as an overhead stream a styrene enriched stream with a styrene content of more than 99.8% by weight. Despite being of high purity, this stream is of inferior quality due to the presence of color causing species, sulfur molecules and oxygenates. As illustrated in the subsequent experimental section, the application of the crystallization block on this stream 10 converts this stream into high quality styrene product or very high quality styrene product (VHPS) as desired by operator. However, during the crystallization performed in the crystallization block 10 as described in detail above, the impurities and in particular different impurities having a boiling point close to that of styrene, such as phenylacetylene, meta- and ortho-xylenes, ethylbenzene, cumene, n-propylbenzene, alpha-methylstyrene and ethyltoluene, are removed. This phenomenon can be exploited to minimize both styrene loss across the phenylacetylene hydrogenation reactor 44 and utility consumption in the upstream distillation columns 40, 42, 46, 48. Removal of phenylacetylene via crystallization enables the phenylacetylene hydrogenation reactor 44 to be operated under low severity conditions or even eliminated altogether. The associated styrene loss during hydrogenation is thereby minimized or non-existent. Removal of close boiling $C_{9+}$-compounds, such as cumene, n-propylbenzene etc., implies that the distillation column 42 or deoctanizer, respectively, in the plant 11 can be relaxed to allow slippage of $C_{9+}$-compounds in the $C_8$-cut. These $C_{9+}$-compounds, by virtue of their polarity and boiling point, will predominantly land in the crude styrene stream and will eventually be removed via the crystallization block 10. Removal of compounds having a boiling point close to that of styrene, such as ethylbenzene, ortho-xylene and meta-xylene, implies that the extractive distillation column 46 and solvent recovery distillation column 48 can be designed with lower solvent to feed ratio and lower extractive distillation column bottoms temperature, thereby lowering capital investment and utility consumption. The purified styrene composition is withdrawn via the discharge conduit 22, whereas the styrene depleted residue fraction obtained in the crystallization block 10 is withdrawn via the discharge conduit 28 together with the $C_8$-raffinate obtained as overhead product of the extractive distillation column 46.

The crystallization block 10 removes, as described in detail above, impurities including color causing species, such as conjugated diolefins, sulfur species, which are primarily $C_6$ thiophenes, and oxygenates, such as water, ketones, aldehydes and alcohols etc. Moreover, the crystallization block, due to the cryogenic nature of the process, prevents unwanted polymer formation in the styrene product. A common problem encountered in adsorbent based styrene treatment is unwanted polymer formation due to localized exotherm at the active sites despite insignificant temperature rise across the beds.

Figure 3:
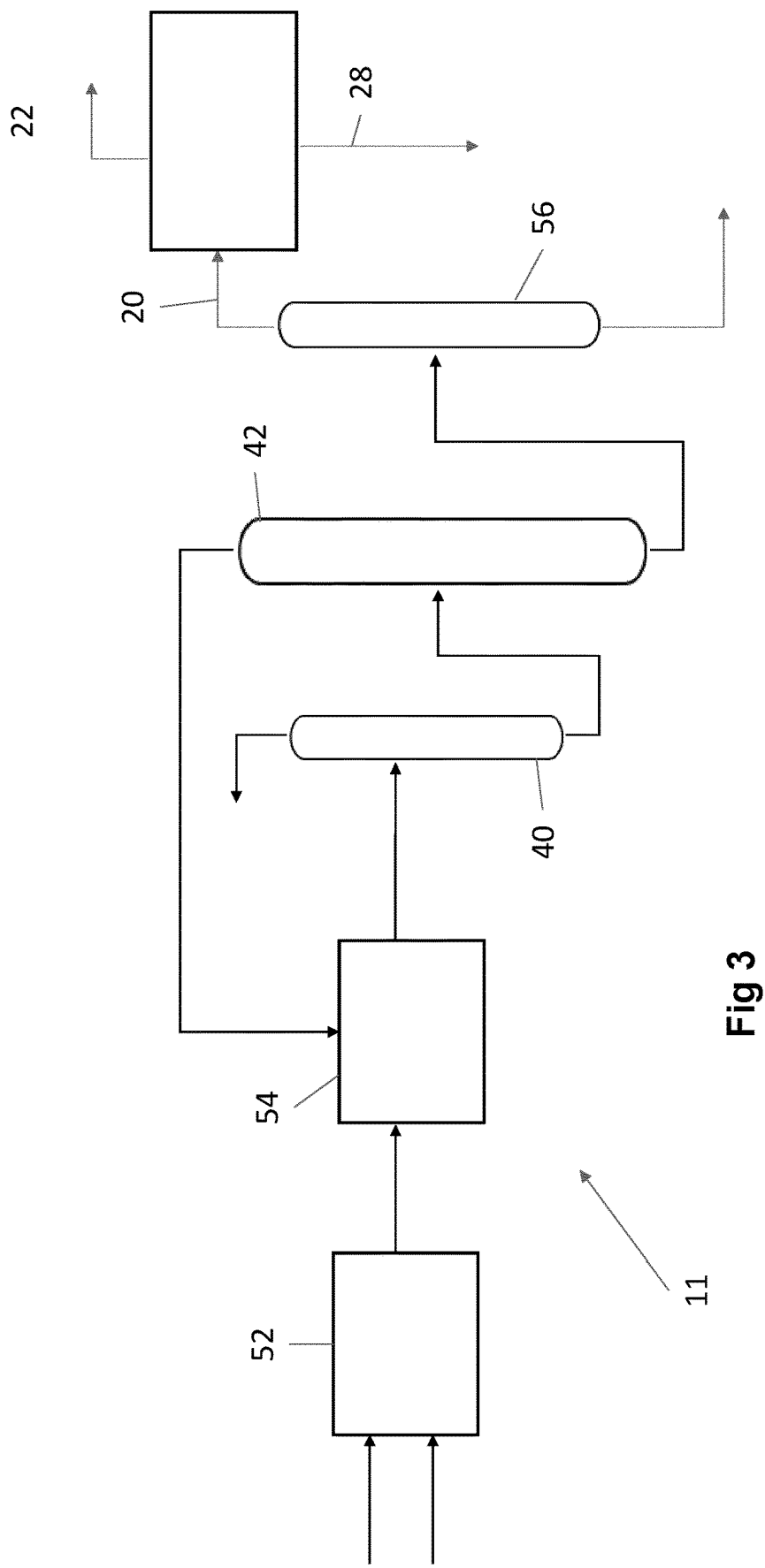
FIG. 3 is a diagrammatic illustration of a plant particularly suitable for purifying an EBSM process stream in accordance with an embodiment of the present disclosure.

FIG. 3 depicts a plant 11 particularly suitable for purifying an EBSM process stream. The plant 11 comprises an alkylation unit 52, a dehydrogenation unit 54, a first distillation column 40, a second distillation column 42, a third distillation column 56 and a crystallization block 10. The crystallization block 10 is composed as that shown in FIG. 1a, as that shown in FIG. 1b or as that shown in FIG. 1c.

During the operation, benzene and ethylene are alkylated in the alkylation reactor 52 to produce ethylbenzene, which is fed into the dehydrogenation reactor 54. The effluent of the dehydrogenation reactor 54 is fed into a separation block which includes the three distillation columns 40, 42, 56. The first distillation column 40 removes benzene and toluene from the effluent of the dehydrogenation reactor 54, whereas the second distillation column 42 separates unreacted ethylbenzene from styrene and the third distillation column 56 distills the styrene stream. The bottom product of the third distillation column 56 is a styrene tar residue produced due to unwanted polymerization of heat sensitive styrene in second distillation column 42. The second distillation column 42 is the largest energy consumer in this system. This is because separation of ethylbenzene from styrene is difficult due to i) close boiling points and ii) heat sensitivity of styrene, which require the column to be operated under vacuum and with a large number of distillation stages. The crystallization in the crystallization block 10 not only effects energy savings, but also reduces unwanted polymerization of styrene in the bottom of the EB distillation column 42. The EB distillation column 42 can be run in a relaxed mode, wherein small amounts of ethylbenzene (up to 3-5% by weight) can drop into the column bottoms. This will not only result in lesser utility consumption or theoretical stages, but also lower bottoms temperature, which implies less unwanted styrene polymerization thereby increasing styrene yield of the overall EBSM process. The ethylbenzene in EB distillation column 42 bottoms will, by virtue of its boiling point, land in the overhead product of the third column 56. This crude styrene containing composition, when fed into the crystallization block 10, will result in production of two streams, namely i) the purified styrene composition withdrawn from the crystallization block 10 via the discharge conduit 22 and ii) an ethylbenzene-rich residue liquor 28, which is sent to the battery limit.

Figure 4:
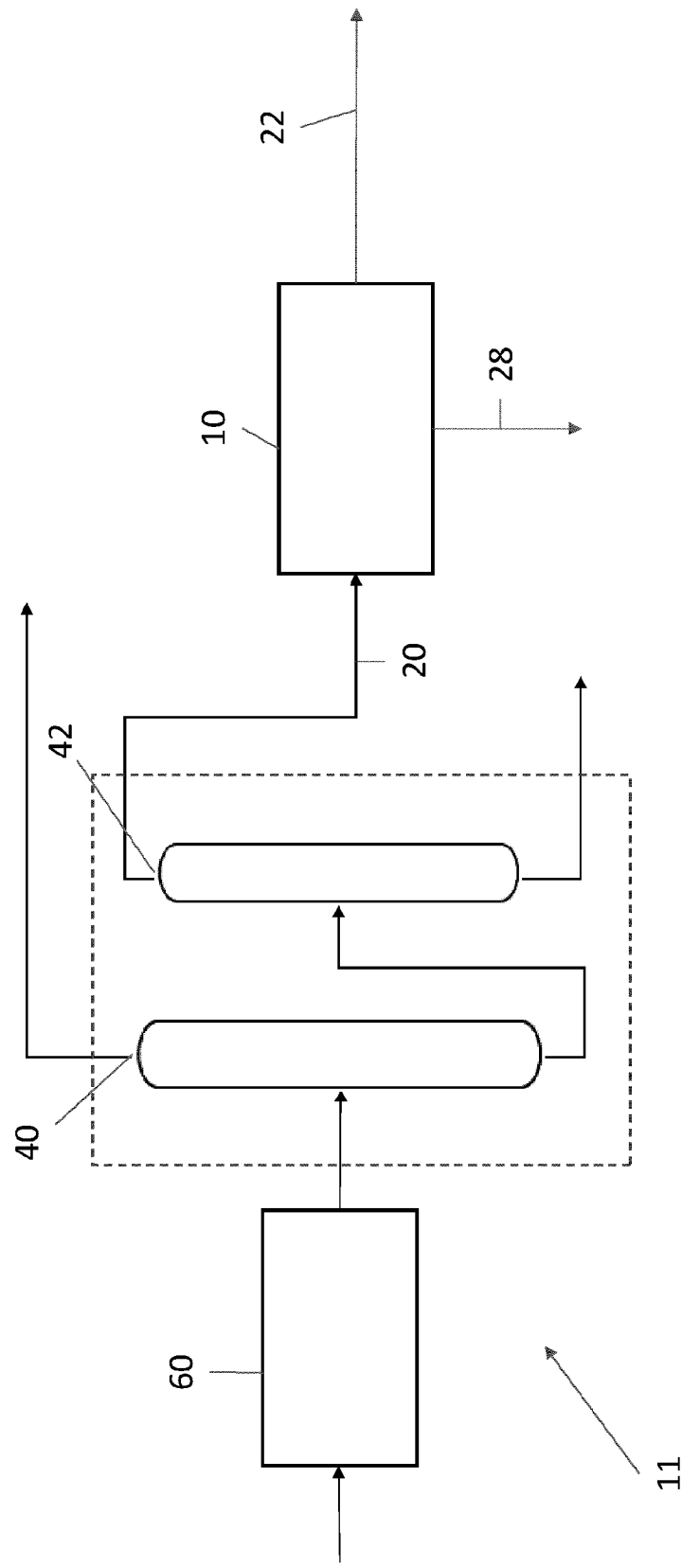
FIG. 4 is a diagrammatic illustration of a plant particularly suitable for purifying a styrene containing stream produced from a polystyrene stream via pyrolysis in accordance with another embodiment of the present disclosure.

FIG. 4 shows a plant 11 particularly suitable for purifying a styrene containing stream produced from a polystyrene stream via pyrolysis. The plant 11 comprises a pyrolysis reactor 60, a first distillation column 40, a second distillation column 42 and a crystallization block 10. The crystallization block 10 is composed as that shown in FIG. 1a, as that shown in FIG. 1b or as that shown in FIG. 1c.

During the operation, the pyrolysis of polystyrene is performed in the pyrolysis reactor, which may be operated thermally or in a catalytic mode. Table 3 gives a typical breakdown of the effluent from the pyrolysis reactor 60 obtained from different methods. The reactor effluent undergoes a series of fractionation steps in the first distillation column 40 and in the second distillation column 42 so as to produce the crude styrene containing composition, which is fed into the crystallization block 10. The crystallization block 10 is applied on the tail end of the distillation step to produce a high purity grade styrene product or VHPS, as desired by operator, at reduced specific energy consumption and capital expenditure.

TABLE 3

Aromatic compounds identified in the liquid fraction of the thermal and catalytic pyrolysis of model polystyrene and commercial products based on polystyrene (wt. % of liquid produced).

| Compounds, chemical formula | Thermal (PS1) | Catalytic BaO (PS2) | Catalytic FCC (PS3) | Plastic container (PS4) | Plastic glass (EPS) (PS5) |
|---|---|---|---|---|---|
| Styrene (monomer) | 63.9 | 69.6 | 45.1 | 53.3 | 70.0 |
| Benzene | — | — | 1.9 | — | 0.1 |
| Toluene | 2.0 | 2.4 | 3.1 | 5.6 | 2.5 |

TABLE 3-continued

Aromatic compounds identified in the liquid fraction of the thermal and catalytic pyrolysis of model polystyrene and commercial products based on polystyrene (wt. % of liquid produced).

| Compounds, chemical formula | Thermal (PS1) | Catalytic BaO (PS2) | Catalytic FCC (PS3) | Plastic container (PS4) | Plastic glass (EPS) (PS5) |
|---|---|---|---|---|---|
| Ethylbenzene 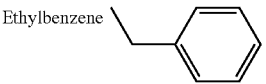 | 0.5 | 1.1 | — | 1.9 | 1.5 |
| α-Methylstyrene 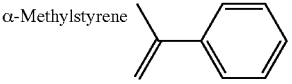 | 2.1 | 2.6 | 6.3 | 5.9 | 2.3 |
| Xylene 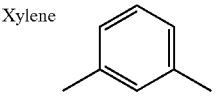 | — | — | 16.8 | — | — |
| Cumene 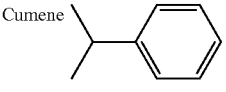 | — | — | 1.7 | 0.2 | 0.3 |
| 2,4-Diphenyl-1-butene (dimer) 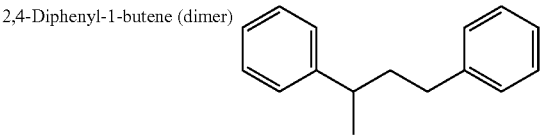 [SMILES: CC(CCc1ccccc1)c1ccccc1] | 14.0 | 18.4 | 1.9 | 11.9 | 9.0 |
| Indane, Indene, etc. 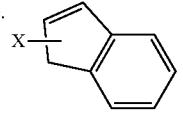 | 2.0 | 0.3 | 5.0 | 2.5 | 0.2 |
| 1,2-Diphenylethane 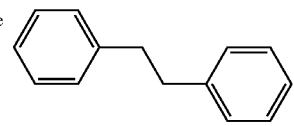 | 2.2 | 0.7 | 0.9 | 2.1 | 0.8 |
| 1-Methyl-1,2-diphenylethane 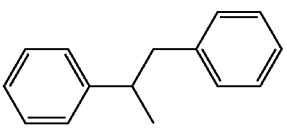 | 1.1 | 0.4 | 0.5 | 1.4 | 0.4 |
| 1,3-Diphenylpropane 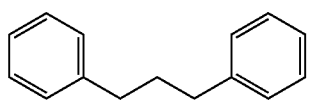 | 0.6 | 0.6 | 0.5 | 2.8 | 0.8 |
| 1,1′-Diphenylpropene 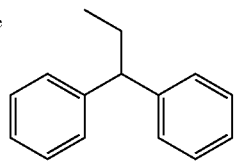 | 0.7 | 0.4 | 1.1 | — | 0.7 |
| Naphthalene and derivatives 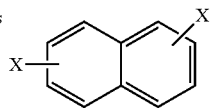 | 0.1 | — | 1.2 | — | — |

TABLE 3-continued

Aromatic compounds identified in the liquid fraction of the thermal and catalytic pyrolysis of model polystyrene and commercial products based on polystyrene (wt. % of liquid produced).

| Compounds, chemical formula | | Thermal (PS1) | Catalytic BaO (PS2) | Catalytic FCC (PS3) | Plastic container (PS4) | Plastic glass (EPS) (PS5) |
|---|---|---|---|---|---|---|
| 2,4,6-Triphenyl-1-hexene (trimer) | 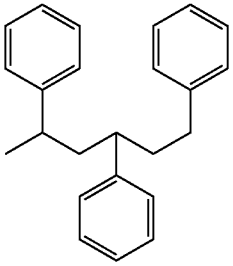 | 2.2 | 1.8 | 0.3 | 3.5 | 5.0 |
| Phenanthrene and derivatives | 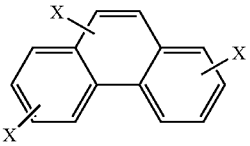 | 0.2 | — | 4.7 | 0.4 | 0.3 |
| Other aromatic compounds | | 8.4 | 1.7 | 9.0 | 8.5 | 6.1 |

Experimental Example

The following example is provided to illustrate the disclosure and does not limit the scope of the claims. Unless stated otherwise, all parts and percentages are by weight. A crude styrene stream, as shown in Table 4, containing different impurities was produced by an extractive distillation unit on pyrolysis gasoline and subsequently purified by means of layer melt crystallization to prepare the final VHPS product and final residue (as shown in FIG. 1b, but using the results of static crystallization instead of a combination of falling film and static (all data based on 20V1980)). The styrene recovery across the crystallization block was >95%.

The term "at least one of" is meant to cover combinations of the listed elements, components, features, and the like, and the listed elements, components, features, and the like individually. For example, the phrase "at least one of A and B" is used to cover embodiments comprising only A, comprising only B, and comprising A and B unless stated otherwise.

The term "comprising" is intended to mean "including at least" such that the recited listing of elements in a claim are an open group. The terms "a," "an" and other singular terms are intended to include the plural forms thereof unless specifically excluded.

TABLE 4

| PEAK ID | UNITS | CRUDE STYRENE | PRODUCT | RESIDUE |
|---|---|---|---|---|
| ETHYLBENZENE | ppm wt | 7 | | |
| CUMENE | ppm wt | 21979 | 2 | 172541 |
| O-XYLENE | ppm wt | 473 | | 3691 |
| N-PROPYLBENZENE | ppm wt | 174 | | 1439 |
| M-ETHYLTOLUENE | ppm wt | 22 | | 235 |
| α-METHYLSTYRENE | ppm wt | 8 | | 277 |
| PHENYLACETYLENE | ppm wt | 9659 | 171 | 57895 |
| 4-METHYLSTYRENE | ppm wt | | | 72 |
| 3-ETHYLTHIOPHENE | ppm S | 0.4 | 0.02 | 2 |
| 2,3-DIMETHYLTHIOPHENE | ppm S | 2 | 0.02 | 14 |
| 3,4-DIMETHYLTHIOPHENE | ppm S | 7 | 0.11 | 60 |
| 2-VINYLTHIOPHENE | ppm S | 30 | 3 | 137 |
| 3-VINYLTHIOPHENE | ppm S | 3 | 2 | 5 |
| SUBSTITUTED THIOPHENE | ppm S | 2 | | 13 |
| SUBSTITUTED THIOPHENE | ppm S | 18 | | 145 |
| PURITY | wt % | 96.63 | 99.98 | 75.39 |
| COLOR | Pt—Co scale | 500 | 10 | >500 |
| OXYGENATES | ppm wt | 200 | <20 | >2000 |

The invention claimed is:

1. A method for preparing a purified styrene composition, the method comprising:
   providing a crude composition containing 70% by weight or more of styrene based on a total weight of the crude composition, and
   subjecting the crude composition to at least one crystallization step to produce a purified styrene, wherein:
   the at least one crystallization step comprises at least one of a static crystallization stage and a dynamic crystallization stage, and
   the crude composition contains at least one impurity selected from the group consisting of: color inducing species, oxygenates, sulfur species, alpha-methylstyrene, and mixtures thereof.

2. The method of claim 1, wherein each of the at least one impurity has a higher melting point than styrene.

3. The method of claim 1, wherein the at least one impurity includes at least one of:
   one or more sulfur species selected from the group consisting of: alkyl, naphthenic or aromatic mercaptans, alkyl, naphthenic or aromatic disulfides, alkyl, aromatic, naphthenic or vinyl thiophenes, oxygenated sulfur containing hydrocarbon compounds, any other hydrocarbon compound including at least one sulfur atom in its molecule, and mixtures thereof, and
   one or more color inducing species selected from the group consisting of: fulvenes, conjugated diolefins, oxygenated species, oxygenated sulfur species, styrene oligomers, alkynes and hydrocarbon compounds comprising conjugated olefin and alkyne bonds, and any other compound imparting a color of more than 10 as defined on Pt-Co scale to styrene.

4. The method of claim 1, wherein the crude composition contains 10 to 30% by weight, based on the total weight of the crude composition, of the at least one impurity.

5. The method of claim 1, wherein the crude composition further contains at least one impurity selected from the group consisting of: meta-xylenes, ortho-xylenes, ethylbenzene, phenylacetylene, cumene, n propylbenzene, ethyltoluene, organo-chlorinated and organo-nitrogenated species, and mixtures thereof.

6. The method of claim 1, wherein the at least one crystallization step comprises at least one static melt crystallization stage, at least one falling film melt crystallization stage, at least one suspension melt crystallization stage or a combination of two or more thereof.

7. The method of claim 1, wherein:
   the at least one crystallization step comprises at least one static crystallization stage and at least one dynamic crystallization stage, and
   the at least one dynamic crystallization stage includes at least one of: at least one falling film crystallization stage and at least one suspension crystallization stage.

8. The method of claim 1, wherein:
   providing the crude composition comprises subjecting a feed composition to at least one of: one or more distillation steps and one or more extractive distillation steps, and
   the crude composition is obtained as a head stream, as a side stream or as a bottom stream of one of the at least one of: one or more distillation steps and one or more extractive distillation steps.

9. The method of claim 1, wherein the crude composition derives from a pygas, and:
   the crude composition has been prepared by distilling a pygas feed composition so as to obtain a C8-fraction and subjecting the C8-fraction to an extractive distillation in which the C8-fraction is treated with a polar solvent so as to obtain a styrene containing fraction as an overhead stream, as a side stream or as a bottom stream, which is used as the crude composition or which is processes into the crude composition, or
   the crude composition has been prepared by distilling a pygas feed composition so as to obtain a C8-fraction, feeding the C8-fraction into a hydrogenation reactor so as to obtain a hydrogenated gas, subjecting the hydrogenated gas to an extractive distillation in which the hydrogenated gas is treated with a polar solvent so as to obtain a styrene containing fraction as an overhead stream, as a side stream or as a bottom stream, which is used as the crude composition or which is processes into the crude composition.

10. The method of claim 1, wherein the crude composition derives from naphtha cracked pyrolysis gasoline.

11. The method of claim 1, wherein the purified styrene composition has a styrene content of at least 99.00% by weight.

12. The method of claim 1, wherein the purified styrene composition satisfies at least one of the following conditions:
    has a color of maximum 15 as defined by Pt-Co scale as per ASTM D5386,
    comprises less than 2 ppmw of total elemental sulfur as contained in mercaptans, disulfides and thiophenes,
    comprises less than 20 ppmw of oxygenates,
    comprises less than 40 ppmw of impurities selected from the group consisting of: phenylacetylene, mixed xylenes, ethylbenzene, cumene, ethyltoluene, n-propylbenzene, and alpha-methyl styrene,
    has a polymer content of less than 10 ppmw, and
    has a total organic chlorine content of less than 2 ppmw.

* * * * *